(12) United States Patent
Hata et al.

(10) Patent No.: US 6,264,970 B1
(45) Date of Patent: *Jul. 24, 2001

(54) SUSTAINED-RELEASE PREPARATION

(75) Inventors: Yoshio Hata, Toyonaka; Hikaru Taira, Ikeda; Jun Sato, Kawanishi; Satoshi Iinuma, Kobe, all of (JP)

(73) Assignee: Takeda Chemical Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/881,143

(22) Filed: Jun. 24, 1997

(30) Foreign Application Priority Data

Jun. 26, 1996 (JP) .................................................. 8-165462

(51) Int. Cl.[7] .................................................. A61K 47/30
(52) U.S. Cl. ........................................ 424/426; 514/772.1
(58) Field of Search ............................... 424/426, 78.17; 530/816; 525/54.1, 54.11; 514/772.1

(56) References Cited

U.S. PATENT DOCUMENTS

| 4,182,654 | * | 1/1980 | Royer . |
| 5,654,381 |   | 8/1997 | Hrkach et al. . |
| 5,733,762 | * | 3/1998 | Midoux et al. . |
| 5,840,338 | * | 11/1998 | Roos et al. . |

FOREIGN PATENT DOCUMENTS

| 42 24 401 A1 | 1/1994 | (DE) . |
| 0 427 190 A2 | 5/1991 | (EP) . |
| 1373660 | 11/1974 | (GB) . |
| WO 94/15587 | 7/1994 | (WO) . |
| 94/21229 | 9/1994 | (WO) . |

OTHER PUBLICATIONS

Y. Kawashima, et al., "Preparation of a Prolonged Release Tablet of Aspirin with Chitosan", Chemical and Pharmaceutical Bulletin, vol. 33, No. 5, May, 1985, pp. 2107–2113.

I. Barakat, et al., "Macromolecular Engineering of Polylactones and Polylactides. X. Selective End–Functionalization of Poly (D,L)—Lactide", Journal of Polymer Science: Part A: Polymer Chemistry, vol. 31, 1993, pp. 505–514.

H. Kim et al., "Studies on Synthesis of Block Copolymers Containing Polyester and Polypeptide for Drug Delivery System", Journal of Korean Chemical Society, vol. 34, No. 2, pp. 203–210, 1990.

M. Gotsche et al., "Amino–termined poly(L–lactide)s as initiators for the polymerization of N–carboxyanhydrides: synthesis of poly(L–lactide)–block–poly($\alpha$–amino acid)s", Macromol. Chem. Phys., vol. 196, pp. 3891–3903, 1995.

P. Degee et al., "Synthesis and Characterization of Biocompatible and Biodegradable Poly($\epsilon$–Caprolactone–b–$\gamma$–Benzylglutamate) Diblock Copolymers", J. Polym. Sci. Part A: Polym. Chem., vol. 31, pp. 275–278, 1993.

* cited by examiner

*Primary Examiner*—Edward J. Webman
(74) *Attorney, Agent, or Firm*—Wenderoth, Lind & Ponack, L.L.P.

(57) ABSTRACT

A sustained-release preparation comprising a bioactive substance having an acidic group and a biodegradable polymer having an optionally protected basic group which improves the rate of incorporation of the bioactive substance, suppresses its leakage early after administration, and exhibits constantly suppressed release for an extended period of time.

3 Claims, No Drawings

US 6,264,970 B1

SUSTAINED-RELEASE PREPARATION

BACKGROUND OF THE INVENTION

1. Field

The present invention relates to a sustained-release preparation comprising a bioactive substance having an acidic group and a biodegradable polymer having an optionally protected basic group.

2. Description of the Related Art

To develop an excellent sustained-release preparation comprising a bioactive substance, various attempts have been made in the field of the manufacturing pharmacy, in consideration of the physical properties of the substance. A currently available method of preparing a sustained-release preparation of a bioactive substance having an acidic group is described in Japanese Patent Unexamined Publication No. 124814/1990, in which an acidic water-soluble drug is encapsuled in a microcapsule having a polymer as the wall material and incorporating a basic substance as a drug-retaining agent.

The Journal of the Korean Chemical Society, Vol. 34, No. 2, pp. 203–210 (1990) describes as a synthesis intermediate a compound wherein 3-amino-1-propanol is bound to the terminal carboxyl group of poly(1-lactide) via ester linkage.

The Journal of Macromol Chem., 196, 3891–3903(1995) discloses a poly(L-lactic acid)—$OCH_2CH_2CH_2$—$NH_2$ and synthesis thereof as a initiator for the polymerization of N-carboxyanhydrides in the synthesis of poly(L-lactide)-block-poly($\alpha$-amino acid)s.

J. POLYM. SCI. PART A: POLYM. CHEM., 31, 275–278 (1993) discloses $\omega$-amino poly($\epsilon$-caprolactone) as a synthesis intermediate.

WO 94/21229 describes an aerosol composition containing a dispersion aid comprising a polymer having an amino acid bound to at least one terminal.

Although serving well as bases for sustained-release preparations of basic drugs, biodegradable polymers such as lactic acid-glycolic acid copolymer are unsatisfactory in terms of bioactivity retention, incorporation rate, suppression of drug leakage early after administration, constant sustained release for an extended period of time, and others, as bases for sustained-release preparations of bioactive substances having an acidic group.

SUMMARY OF THE INVENTION

Through extensive investigation aiming at creating a sustained-release preparation of acidic drug having excellent sustained-release property, the present inventors found that the use of a biodegradable polymer wherein a basic group is introduced as a base for sustained-release preparation results in an improved microcapsule incorporation rate and suppressed leakage early after administration, without loss of the activity of a bioactive substance having an acidic group, and ensures constant sustained release for an extended period of time. The present inventors made further investigation based on this finding, and developed the present invention.

Accordingly, the present invention relates to:

(1) a sustained-release preparation which comprises a bioactive substance having an acidic group and a biodegradable polymer having an optionally protected basic group,
(2) the sustained-release preparation according to term (1) above, wherein the polymer has at least an optionally protected basic group at a terminal,
(3) the sustained-release preparation according to term (1) above, wherein the polymer has an optionally protected basic group which is introduced to the terminal carboxyl group,
(4) the sustained-release preparation according to term (1) above, wherein the polymer has at a terminal a thioesterified, esterified or amidated carboxyl group having an optionally protected basic group,
(5) the sustained-release preparation according to term (1) above, wherein the biodegradable polymer is an aliphatic polyester,
(6) the sustained-release preparation according to term (5) above, wherein the aliphatic polyester is an $\alpha$-hydroxycarboxylic acid polymer,
(7) the sustained-release preparation according to term (5) above, wherein the aliphatic polyester is a homopolymer or copolymer of lactic acid and glycolic acid,
(8) the sustained-release preparation according to term (7) above, wherein the weight-average molecular weight of the homopolymer or copolymer of lactic acid and glycolic acid is not less than about 2,000,
(9) the sustained-release preparation according to term (7) above, wherein the lactic acid/glycolic acid content ratio is about 100/0 to about 30/70 (mol/mol %),
(10) the sustained-release preparation according to term (l), wherein the basic group is (i) a cyclic amino group, (ii) a nucleic acid base or (iii) a hydrocarbon group having 1 to 5 substituents selected from the group consisting of amino groups, amidino groups, guanidino groups, ammonium groups, cyclic amino groups and nucleic acid bases, each of which may be substituted,
(11) A polymer having the formula: POLY-CO—NH—R'—X' wherein POLY represents the principal chain of a polymer, R' represents a divalent hydrocarbon group, X' represents a basic group selected from amino groups, amidino groups, cyclic amino groups and nucleic acid bases each of which basic group may be protected,
(12) the polymer according to term (11) above, wherein POLY is a principal chain of a homopolymer or copolymer of an $\alpha$-hydroxycarboxylic acid,
(13) The polymer according to term (12) above, wherein the $\alpha$-hydroxycarboxylic acid is lactic acid and/or glycolic acid,
(14) the polymer according to term (11) above, wherein R' is a $C_{1-15}$ hydrocarbon group,
(15) the polymer according to term (11), wherein X' is an optionally protected amino group,
(16) a polymer having the formula: POLY-COO—R"—X' wherein POLY represents the principal chain of a homopolymer or copolymer of $\alpha$-hydoxycarboxylic acid, R" represent ethylene which may be substituted with $C_{1-4}$ alkyl; X' represents a basic group selected from amino groups, amidino groups, cyclic amino groups and nucleic acid base, each of which basic group may be protected,
(17) a method of producing the polymer of term (11) above which comprises reacting a compound having the protected basic group of the formula $H_2N$—R'—S' with a polymer of the formula POLY-COOH or active derivative thereof,
(18) the method according to term (17) above, which further comprises deprotection reaction of the protected basic group of the polymer,
(19) a method of improving the sustained-release property of a sustained-release preparation for a bioactive substance having an acidic group by using a biodegradable polymer having an optionally protected basic group as a base thereof,
(20) a base for a sustained-release preparation of a bioactive substance having an acidic group, which comprises a biodegradable polymer having an optionally protected basic group, and

(21) use of a biodegradable polymer having an optionally protected basic group, for the production of a sustained-release preparation of a bioactive substance having an acidic group.

DESCRIPTION OF THE PREFERRED EMBODIMENTS

In the present invention, the "biodegradable polymer" is not subject to limitation, as long as it becomes compatible with living tissue and exhibits no deleterious action on the living body after administration. The biodegradable polymer is more preferably one that is metabolically degraded in vivo and eventually excreted from the body, commonly used such biodegradable polymers including those that are sparingly soluble or insoluble in water. The biodegradable polymer is exemplified by those described in "Drug Delivery System, Chapter 3 (CMC, 1986)." Specifically, useful biodegradable include the following:

(1) Fatty acid polyesters:
(i) Polymers and copolymers synthesized from one or more α-hydroxycarboxylic acids (e.g., glycolic acid, lactic acid, hydroxybutyric acid), hydroxydicarboxylic acids (e.g., malic acid), hydroxytricarboxylic acids (e.g., citric acid) etc., mixtures thereof, β-poly-α-benzyl malate, poly-3-hydroxybutanoic acid.
(ii) Polymers and copolymers synthesized from one or more polylactides (e.g., glycolides, lactides, benzylmalolactonate, malide dibenzyl ester, 3-[(benzyloxycarbonyl)methyl]-1,4-dioxane-2,5-dione) etc., mixtures thereof.
(iii) Polymers and copolymers synthesized from one or more polylactones (e.g., β-propiolactone, δ-valerolactone, ε-caprolactone, N-benzyloxycarbonyl-L-serine-β-lactone) etc., mixtures thereof. These can be copolymerized with glycolides, lactides etc. as cyclic dimers of α-hydroxy acids.
(iv) Polyethylene adipate.
(2) Polyanhydrides(e.g., poly[1,3-bis(p-carboxyphenoxy)methane], poly(terephthalic-sebacic anhydride)).
(3) Polycarbonates (e.g., poly(oxycarbonyloxyethylene), spiro-ortho-polycarbonate).
(4) Poly-ortho-esters (e.g., poly(3,9-bis(ethylidene-2,4,8,10-tetraoxaspiro[5,5]undecane-1,6-hexanediol).
(5) Polyamino acids (e.g., poly-γ-benzyl-L-glutamate, poly-L-alanine, poly-γ-methyl-L-glutamate).
(6) Polyamides (e.g., poly-α,β[N-(2-hydroxyethyl)]-D,L-aspartamide, poly-γ-glutamic acid benzyl ester).
(7) Poly-α-cyanoacrylic acid esters (e.g., isobutyl poly-α-cyanoacrylate).
(8) Polyphosphazenes (e.g., polydiaminophosphazene).
(9) Polydepsipeptides (e.g., 3-[4-(benzyloxycarbonylamino)butyl]-6-methylmorpholine-2,5-dione polymer or its copolymers with lactones (e.g., ε-caprolactone) and lactides (e.g., glycolides, lactides).

These may be used as a mixture in appropriate ratios. Type of polymerization may be random, block or graft. Commonly used examples of the biodegradable polymer include fatty acid polyesters (e.g., polymers and copolymers synthesized from one or more α-hydroxycarboxylic acids (e.g., glycolic acid, lactic acid, hydroxybutyric acid), hydroxydicarboxylic acids (e.g., malic acid), hydroxytricarboxylic acids (e.g., citric acid) etc., or mixtures thereof).

Of the above-mentioned fatty acid polyesters, polymers or copolymers synthesized from one or more α-hydroxycarboxylic acids (e.g., glycolic acid, lactic acid, hydroxybutyric acid) are preferred from the viewpoint of biocompatibility and biodegradability. These copolymers may be used as a mixture in appropriate ratios.

While these α-hydroxycarboxylic acids may be of the D-, L- or D,L-configuration, the D-/L-ratio (mole/mole %) preferably falls within the range from about 75/25 to about 25/75. Especially, α-hydroxycarboxylic acids with a D-/L-ratio, (mole/mole %) within the range from about 60/40 to about 30/70 are desirably used. Copolymers of the α-hydroxycarboxylic acid include, for example, copolymers of glycolic acid and other α-hydroxy acids. Preferable examples of the α-hydroxy acid include lactic acid and 2-hydroxybutyric acid. Examples of preferable copolymers of α-hydroxycarboxylic acids include lactic acid-glycolic acid copolymer and 2-hydroxybutyric acid-glycolic acid copolymer, lactic acid-glycolic acid copolymer being desirably used. Although the content ratio (lactic acid/glycolic acid) (mole/mole %) of the lactic acid-glycolic acid copolymer is not subject to limitation, as long as the objective of the present invention is accomplished, it is normally about 100/0 to about 30/70 (hereinafter the term "lactic acid-glycolic acid copolymer" sometimes refers to both of lactic acid homopolymer (poly lactide) and lactic acid-glycolic acid copolymer (poly (lactide-glycolide)). The content ratio is preferably about 90/10 to about 40/60, for example, content ratios of about 80/20 to about 45/55 being desirably used. The lactic acid-glycolic acid copolymer has a weight-average molecular weight of about 2,000 to about 70,000, for example, with preference given to lactic acid-glycolic acid copolymers whose weight-average molecular weight is about 3,000 to about 20,000. Those having a weight-average molecular weight of about 5,000 to about 15,000 are desirably used. Also, the degree of dispersion (weight-average molecular weight/number-average molecular weight) of the lactic acid-glycolic acid copolymer is preferably about 1.2 to about 4.0, those having a degree of dispersion of about 1.5 to about 3.5 being desirably used.

In the present specification, weight-average molecular weight and the degree of dispersion are defined as that based on polystyrene measured by gel permeation chromatography (GPC). Measurements were taken using a GPC column KF804Lx2 (produced by Showa Denko, Japan) and an RI monitor L-3300 (produced by Hitachi Ltd., Japan) with chloroform as a mobile phase using 9 polystyrenes with the weight average molecular weights of 120,000, 52,000, 22,000, 9,200, 5,050, 2,950, 1,050, 580 and 162 as references and the dispersion value calculated using the same molecular weight, respectively.

The number average molecular weight by end-group determination, is defined as the following manner.

A biodegradable polymer, about 1 to 3 g, was dissolved in a mixture of acetone (25 ml) and methanol (5 ml) and using phenolphthalein as the indicator, the carboxyl groups in the solution were quickly titrated with 0.05N alcoholic potassium hydroxide solution under stirring at room temperature (20° C.).

Then the number average molecular weight by end-group determination was calculated by means of the following equation.

Number average molecular weight by end-group determination= $20000 \times A/B$ where A is the mass of biodegradable polymer (g) and B is the amount of 0.05N alcoholic potassium hydroxide solution (ml) added to react the titration 10 end-point.

Although the 2-hydroxybutyric acid-glycolic acid copolymer is not subject to limitation, as long as the objective of the present invention is accomplished, it is preferable that glycolic acid account for about 10 to about 75 mol % and 2-hydroxybutyric acid for the remaining portion. More preferably, glycolic acid accounts for about 20 to about 75 mol %. Those having a glycolic acid content of about 30 to about 70 mol % are desirably used. The weight-average molecular weight of the 2-hydroxybutyric acid-glycolic acid copolymer is preferably about 2,000 to about 20,000. The degree of dispersion (weight-average molecular weight/ number-average molecular weight) of the 2-hydroxybutyric acid-glycolic acid copolymer is preferably about 1.2 to about 4.0, especially, those having a degree of dispersion of about 1.5 to about 3.5 being desirably used.

Although the α-hydroxybutyric acid is not subject to limitation, as long as the objective of the present invention is accomplished, lactic acid polymers may be mentioned as preferable examples of its polymer. The weight-average molecular weight of the lactic acid polymer is preferably about 2,000 to about 20,000, those having a weight-average molecular weight of about 5,000 to about 15,000 being desirably used.

The 2-hydroxybutyric acid-glycolic acid copolymer may be used as a mixture with polylactic acid. While the polylactic acid may be of the D- or L-configuration or a mixture thereof, the ratio of the D-/L-configuration (mole/mole %) falls within the range from about 75/25 to about 20/80, for example. Preferred are polylactic acids with the D-/L-ratio (mole/mole %) is about 60/40 to about 25/75, those whose ratio of the D-/L-configuration (mole/mole %) is about 55/45 to about 25/75 being desirably used. The polylactic acid has a weight-average molecular weight of about 1,500 to about 20,000, for example, with preference given to those whose weight-average molecular weight is about 1,500 to about 10,000. Also, the degree of dispersion of the polylactic acid is about 1.2 to about 4.0, those having a degree of dispersion of about 1.5 to about 3.5 being desirably used.

When a 2-hydroxybutyric acid-glycolic acid copolymer and polylactic acid are used as a mixture, their mixing ratio is about 10/90 to about 90/10 (% by weight), for example. The mixing ratio is preferably about 20/80 to about 80/20, mixing ratios of about 30/70 to about 70/30 being desirably used.

The above-described biodegradable polymer has a basic group that may be protected. The basic group that may be protected is not subject to limitation, as long as it is a group exhibiting acid-base interaction with the acidic group of a bioactive substance having an acidic group, and having a pKa value of not less than 8 (e.g., the amines described in Dai Yuki Kagaku, Supplement 2, pp. 584–613, which have a dissociation constant of not less than 8). In the present invention, the polymer having a protected basic group is also comparable to use as a base for sustained-release preparation as long as the polymer having a pKa value in the above scope. To more efficiently accomplish the objective of the present invention, however, it is desirable to introduce a basic group that may be protected to a terminal of a biodegradable polymer. More desirably, the basic group that may be protected is introduced to the terminal carboxyl group alone of the biodegradable polymer, or to both terminal carboxyl and hydroxyl groups. The optionally protected basic group is desirably introduced to the biodegradable polymer via ester linkage, thioester linkage or amide linkage, i.e., it desirably has an esterified, thioesterified or amidated terminal carboxyl group. The amide linkage includes

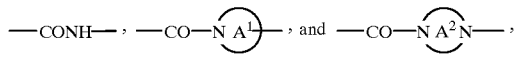

preferably, 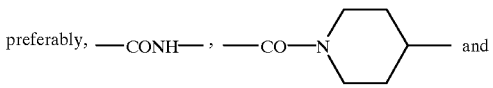

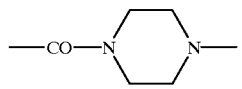

In the above formulas, ring $A^1$ and ring $A^2$ each represent a 5- to 7-membered ring, wherein all atoms but N are carbon atoms. From the viewpoint of acid-base interaction, the basic group introduced to the biodegradable preferably has no protecting groups. When the basic group has a hydroxyl group, an amino group and/or a thiol group, the biodegradable polymer may be bound according to the number of such groups, as long as the spirit of the present invention is not deviated from.

Useful basic groups for the optionally protected basic group include (i) cyclic amino groups or nucleic acid bases or (ii) hydrocarbon groups having 1 to 5 substituents selected from the group consisting of amino groups, amidino groups, guanidino groups, ammonium groups, cyclic amino groups and nucleic acid bases.

The cyclic amino group is exemplified by pyrrolidinyl group, piperidyl group, imidazolidinyl group, imidazolinyl group, pyrazolidinyl group, pyrazolinyl group, piperazinyl group, indolinyl group, isoindolinyl group, quinuclidinyl group and morpholinyl groups.

The nucleic acid base is exemplified by 6-aminopurinyl group, 6-amino-2-purinyloxy group, 4-amino-2-pyrimidinyloxy group, 5-methyl-2,4-pyrimidinyloxy group and 2,4-pyrimidinyloxy group.

The hydrogen present in the amino group, amidino group, guanidino group or ammonium group may be substituted for by the hydrocarbon groups shown below.

The hydrocarbon group is exemplified by alkyl groups, alkenyl groups, alkynyl groups, cycloalkyl groups, aryl groups and aralkyl groups.

The alkyl group is exemplified by $C_{1-24}$ alkyl groups (e.g., methyl, ethyl, n-propyl, isopropyl, n-butyl, 1-methylpropyl, isobutyl, t-butyl, n-pentyl, 1-methylbutyl, n-hexyl, 4-methylpentyl, n-heptyl, 1-propylbutyl, n-octyl, 1-methylheptyl, 1-propylpentyl, n-nonyl, n-decyl, undecyl, dodecyl, tridecyl, tetradecyl, pentadecyl, 1-propylhexyl, 1-methyloctadecyl, hexylethyl, 4-ethyl-5-methyloctyl, 4-isopropyl-5-propyldecyl). The alkyl group may have 1 to 3 $C_{2-15}$ alkenyl groups (e.g., vinyl), $C_{2-6}$ alkynyl groups (e.g., ethynyl), $C_{3-6}$ cycloalkyl groups (e.g., cyclohexyl), $C_{6-10}$ aryl groups (e.g., phenyl), $C_{7-14}$ aralkyl groups (e.g., benzyl) etc in appropriate positions thereof. Examples of such alkyl groups include vinylethyl and benzylethyl.

The alkenyl group is exemplified by $C_{2-15}$ alkenyl groups (e.g., vinyl, 1-propenyl, allyl, isopropenyl, 1-butenyl, 2-butenyl, 3-butenyl, 1-pentenyl, 2-pentenyl, 1-hexenyl, 2-hexenyl, 1-heptenyl, 1-octenyl, nonenyl, 2-methylpropen-1-yl, 1-methylpropen-1-yl, 1-methylallyl, 2-methylallyl, dimethylhexenyl, 4-propyl-2-pentenyl, 1-dodecenyl, 1-tridecenyl, 2-nonyl-2-butenyl).

The alkynyl group is exemplified by $C_{2-6}$ alkynyl groups (e.g., ethynyl, 1-propynyl, 2-propynyl).

The cycloalkyl group is exemplified by $C_{3-10}$ cycloalkyl groups (e.g., cyclobutyl, cyclopentyl, cyclohexyl, cycloheptyl, cyclooctyl, cyclononyl).

The aryl group is exemplified by $C_{6-14}$ aryl groups (e.g., phenyl, tolyl, naphthyl).

The aralkyl group is exemplified by $C_{7-16}$ aralkyl groups (e.g., benzyl, phenethyl).

The above mentioned alkenyl group, alkynyl group, cycloalkyl group, aryl group and aralkyl group may be substituted with 1 to 3 $C_{1-10}$ alkyl groups, $C_{2-10}$ alkenyl groups, $C_{3-10}$ cycloalkyl groups, $C_{6-10}$ aryl groups or $C_{7-14}$ aralkyl groups at appropriate position thereof.

The above-described basic group is introduced to a biodegradable compound via, for example, ester linkage, thioester linkage or amide linkage.

The amino group, amidino group, guanidino group, ammonium group, cyclic amino group or nucleic acid base may have the protecting groups shown below.

Protecting groups that may be present in the basic group include, for example, the protecting groups described on page 2,555 and thereafter in Shin Jikken Kagaku Koza, Vol. 14, published by Maruzen, Japan but are not subject to limitation, as long as the desired biodegradable polymer is obtained. Useful protecting groups include, for example, acyl derivatives (e.g., formyl, acetyl, benzoyl), urethane type derivatives [e.g., benzyloxycarbonyl, t-butoxycarbonyl, 2-(p-biphenyl)isopropoxycarbonyl, diisopropylmethyloxycarbonyl, piperidinoxycarbonyl, β-(p-toluenesulfonyl)ethoxycarbonyl, β-iodoethoxycarbonyl, 8-quinolinyloxycarbonyl, β,β,β-trichloroethoxycarbonyl, isobutyloxycarbonyl, cyclopentyloxycarbonyl, cyclohexyloxycarbonyl, L-menthyloxycarbonyl, 1-adamantanyloxycarbonyl, 4-methoxybenzyloxycarbonyl, 4-decyloxybenzyloxycarbonyl, 4-nitrobenzyloxycarbonyl, furfuryloxycarbonyl, diphenylmethoxycarbonyl, 9-fluorenylmethoxycarbonyl], alkyl derivatives (e.g., thiophenoxycarbonyl, thiobenzyloxycarbonyl), alkenyl derivatives (e.g., allyl), aryl derivatives (e.g., 2,4-dinitrophenyl, tetrahydropyranyl), N-nitroso derivatives (e.g., nitroso), N-nitro derivatives (e.g., nitro), phosphoryl derivatives (e.g., benzylphosphoryl, diphenylphosphoryl), sulfenyl derivatives (e.g., arylsulfinyl, triphenylmethylsulfenyl, 3-nitro-2-pyridinesulfenyl), sulfonyl derivatives (e.g., benzylsulfonyl, arylsulfonyl) and trialkyl derivatives.

Preferably, the terminal carboxyl group of the biodegradable polymer has N-benzyloxycarbonyl-aminomethanol, 2-(N-benzyloxycarbonyl)-aminoethanol, 2-(N-benzyloxycarbonyl)amino-4-methyl-pentan-1-ol, 2-(N-benzyloxycarbonyl)amino-3-phenyl-propan-1-ol, 2-(N-t-butoxycarbonyl)amino-3-phenyl-propan-1-ol, 2-(t-butoxycarbonyl)amino-3-methyl-butan-1-ol, 2-(N-t-butoxycarbonyl)amino-4-methyl-pentan-1-ol, 2-(N-t-butoxycarbonyl)amino-3-methyl-pentan-1-ol, 2-(N-t-butoxycarbonyl)amino-3-phenyl-propan-1-ol, 2-(benzyloxycarbonyl)amino-4-(t-butoxycarbonyl)-butan-1-ol, 1-aminopropan-2-ol, 1-aminopropan-3-ol, 1-aminobutan-2-ol, 1-amino-3-buten-2-ol, 2-aminobutan-1-ol, 2-aminobutan-3-ol, 1-amino-2-methylpropan-2-ol, 2-amino-2-methylpropan-1-ol, 2-aminohexan-1-ol, 3-aminoheptan-4-ol, 1-aminooctan-2-ol, 5-aminooctan-4-ol, 3-aminononan-4-ol, 1-aminopropan-3-ol, 3-aminobutan-1-ol, 1-aminobutan-4-ol, 1-aminopentan-5-ol, 1,2-diaminopropan-3-ol, 1,3-diaminopropan-2-ol, 1-amino-2,2-bis(aminomethyl)propan-1-ol, N-(2-hydroxyethyl)ethylenediamine, N-(2-hydroxypropyl)ethylenediamine, N-(2-hydroxy-2-methylpropyl)ethylenediamine, 1-aminopropane-2,3-diol, 2-aminopropane-1,3-diol, 2-amino-2-methylpropane-1,3-diol, 2-amino-2-ethylpropane-1,3-diol, 2-amino-2-oxymethylpentan-1-ol, 2-amino-2-oxymethyl-3-methylbutan-1-ol, tris(hydroxymethyl)aminomethane, 1-amino-2,2-bis(oxymethyl)propan-3-ol, 2,2-bis(aminomethyl)propane-1,3-diol, 1-amino-2,2-bis(aminomethyl)propan-1-ol, N-(2-hydroxyethyl)ethylenediamine, N-(2-hydroxypropyl)ethylenediamine, N-(2-hydroxy-2-methylpropyl)ethylenediamine, N-monobenzyloxycarbonylaminal, N-monobenzyloxycarbonyl(n-propyl)aminal, N-monobenzyloxycarbonyl(i-propyl)aminal, N-monobenzyloxycarbonyl(i-butyl)aminal, N-monobenzyloxycarbonyl(benzyl)aminal, N-monobenzyloxycarbonyl-ethylenediamine, 3-(t-butoxycarbonylamino)-3-benzylpropylamine, 3-(t-butoxycarbonylamino)-3-(i-butyl)propylamine, 3-(benzyloxycarbonylamino)propylamine, 2-benzyloxycarbonylaminoethanethiol or the like, for example, introduced thereto.

With respect to the biodegradable polymer having an optionally protected basic group for the present invention, it is desirable that the effect of the basic group surpasses that of the acidic group, and that no groups showing acidity are contained.

Preferable examples of the biodegradable polymer having an optionally protected basic group for the present invention include those represented by the structural formulas shown below.

(Ia)

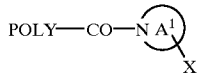
(Ib)

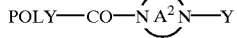
(Ic)

(Id)

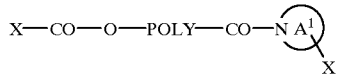
(Ie)

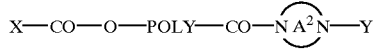
(If)

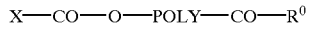
(Ig)

In formula (Ia), POLY represents the principal chain of the biodegradable polymer; A represents O, NH or S; X represents (i) a cyclic amino group or a nucleic acid base or (ii) a hydrocarbon group having 1 to 5 substituents selected from the group consisting of amino groups, amidino groups, guanidino groups, ammonium groups, cyclic amino groups and nucleic acid bases.

In formula (Ib), POLY represents the principal chain of the biodegradable polymer; X represents (i) a cyclic amino group, (ii) a nucleic acid base or (iii) a hydrocarbon group having 1 to 5 substituents selected from the group consisting of amino groups, amidino groups, guanidino groups, ammonium groups, cyclic amino groups and nucleic acid bases; ring $A^1$ is a 5- to 7-membered ring.

In formula (Ic), POLY represents the principal chain of the biodegradable polymer; Y represents (i) a hydrogen atom, (ii) a cyclic amino group, (iii) a nucleic acid base or (iv) a hydrocarbon group having 1 to 5 substituents selected from the group consisting of amino groups, amidino groups, guanidino groups, ammonium groups, cyclic amino groups and nucleic acid bases; ring $A^2$ is a 5- to 7-membered ring.

In formula (Id), POLY represents the principal chain of the biodegradable polymer; A represents O, NH or S; X represents (i) a cyclic amino group, (ii) a nucleic acid base or (iii) a hydrocarbon group having 1 to 5 substituents selected from the group consisting of amino groups, amidino groups, guanidino groups, ammonium groups, cyclic amino groups and nucleic acid bases.

In formula (Ie), POLY represents the principal chain of the biodegradable polymer; X represents (i) a cyclic amino group, (ii) a nucleic acid base or (iii) a hydrocarbon group having 1 to 5 substituents selected from the group consisting of amino groups, amidino groups, guanidino groups, ammonium groups, cyclic amino groups and nucleic acid bases; ring $A^1$ is a 5- to 7-membered ring.

In formula (If), POLY represents the principal chain of the biodegradable polymer; X represents (i) a cyclic amino group, (ii) a nucleic acid base or (iii) a hydrocarbon group having 1 to 5 substituents selected from the group consisting of amino groups, amidino groups, guanidino groups, ammonium groups, cyclic amino groups and nucleic acid bases; Y represents (i) a hydrogen atom, (ii) a cyclic amino group, (iii) a nucleic acid base or (iv) a hydrocarbon group having 1 to 5 substituents selected from the group consisting of amino groups, amidino groups, guanidino groups, ammonium groups, cyclic amino groups and nucleic acid bases; ring $A^2$ is a 5- to 7-membered ring.

In formula (Ig), POLY represents the principal chain of the biodegradable polymer; X represents (i) a cyclic amino group, (ii) a nucleic acid base or (iii) a hydrocarbon group having 1 to 5 substituents selected from the group consisting of amino groups, amidino groups, guanidino groups, ammonium groups, cyclic amino groups and nucleic acid bases; $R^0$ represents a hydrocarbon group.

The principal chain of biodegradable polymer represented by POLY means the principal chain moiety of the above-described biodegradable polymer.

The cyclic amino group, nucleic acid base and hydrocarbon group having 1 to 5 substituents selected from the group consisting of amino groups, amidino groups, guanidino groups, ammonium groups, cyclic amino groups and substituents represented by X and Y mean the same groups as those mentioned above. These groups may be protected by the same protecting groups as those mentioned above.

The hydrocarbon group represented by $R^0$ is exemplified by the same hydrocarbon groups as those mentioned above.

POLY is preferably the principal chain of a polymer or copolymer of an α-hydroxycarboxylic acid (the same as those mentioned above), principal chains of lactic acid-glycolic acid copolymers (the same as those mentioned above) being commonly used.

A is preferably O or NH.

X and Y are preferably hydrocarbon groups having 1 to 3 amino groups that may be protected. The amino group protecting group and hydrocarbon group are exemplified by the same groups as those mentioned above.

In the present invention, biodegradable polymers represented by formula (Ia) are preferred. In the formula (Ia), the group represented by —A—X is preferably the group of the formula —NH—R'—X' or —O—R"—X', wherein R' and R" are a divalent hydrocarbon group and X' is an amino, amidino, guanidino, ammonium, cyclic amino group or nucleotide base which may be protected, preferably an optionally protected amino group. The divalent hydrocarbone group represented by R' and R" are derived from the hydrocarbon group as mentioned above.

Examples of the divalent hydrocarbon group represented by R' include $C_{1-15}$ alkylene (e.g. methylene, ethylene, propylen, tetramethylen, 3,3-dimethylpentamethylene, etc.), $C_{2-15}$ alkenylene (e.g. vinylene, propenylene, methylpropenylene, dimethylpropenylene etc.), $C_{3-10}$ cycloalkylene (e.g. cycloalpropylene, 1,3-cyclopentylene, 3-cyclohexen-1,2-ylene etc.) and $C_{6-10}$ arylene (e.g. phenylene, mophtylene etc.), wherein these groups may be substituted with 1 to 3 $C_{1-4}$ alkyl, $C_{2-4}$ alkenyl, $C_{3-10}$ cycloalkyl and $C_{6-10}$ aryl groups in appropriate positions thereof. R' is preferably, $C_{1-10}$ divalent hydrocarbon group, more preferably $C_{1-8}$ divalent hydrocarbon group. $C_{1-9}$ alkylene is a preferable embodiment of R'.

R" is preferably ethylene which may be substituted with $C_{1-4}$ alkyl.

Preferable examples of the group represented by —A—X include aminomethyloxy group, 2-aminoethyloxy group, 1-aminopropan-2-oxy group, 1-aminopropan-3-oxy group, 1-aminobutan-2-oxy group, 1-amino-3-buten-2-oxy group, 2-aminobutan-1-oxy group, 2-aminobutan-3-oxy group, 3-aminobutan-1-oxy group, 1-aminobutan-4-oxy group, 1-amino-2-methylpropan-2-oxy group, 2-amino-2-methylpropan-1-oxy group, 1-aminopentan-5-oxy group, 2-aminohexan-1-oxy group, 3-aminoheptan-4-oxy group, 1-aminooctan-2-oxy group, 5-aminooctan-4-oxy group, 3-aminononan-4-oxy group, 1,2-diaminopropan-3-oxy group, 1,3-diaminopropan-2-oxy group, 1-amino-2,2-bis (aminomethyl)propan-1-oxy group, 1,2-diaminopropan-2-oxy group, 2-(2-aminoethyl)aminoethyloxy group, 3-(2-aminoethyl)aminopropan-2-oxy group, 3-aminopropane-1,2-dioxy group, 2-aminopropane-1,3-dioxy group, 2-amino-2-methylpropane-1,3-dioxy group, 2-amino-2-propylpropane-1,3-dioxy group, 2-amino-2-(1-methyl) ethylpropane-1,3-dioxy group, aminomethane-tris (methoxy) group, 2-aminoethane-tris(methoxy) group, 2,2-bis(aminomethyl)propane-1,3-dioxy group, aminomethylamino group, 1-aminobutylamino group, 1-amino-2-methylpropylamino group, 1-amino-3-methylbutylamino group, 1-amino-2-phenylethylamino group, 2-aminoethylamino group, 3-amino-4-phenylbutylamino group, 3-amino-5-methylhexylamino group, 3-aminopropylamino group, 2-aminoethylthio group, 2-amino-2-methylethyloxy group, 2-amino-2-(1-methylethyl)ethyloxy group, 2-amino-2-(2-methylpropyl) ethyloxy group, 2-amino-2-(1-methylpropyl)ethyloxy group, 2-amino-2-benzylethyloxy group, 2-aminobutane-1,3-dioxy group, 2-amino-2-(4-aminobutyl)ethyloxy group, 2,6-diaminohexane-1,5-dioxy group, 2-amino-2-(3-guanidinopropyl)ethyloxy group, 2-amino-2-(carbamoylmethyl)ethyloxy group, 2-amino-2-(2-carbamoylethyl)ethyloxy group, 2-amino-2-(2-methylthioethyl)methylethyloxy group, 2-amino-2-(oxyphenylmethyl)methylethyloxy group, 2-amino-2-(5-imidazolylmethyl)ethyloxy group and 2-amino-2-(3-indolylmethyl)ethyloxy group.

More preferable examples of the biodegradable polymer having an optionally protected basic group for the present invention include (i) lactic acid-glycolic acid copolymers wherein a compound containing a mono- or di-aminoalkyl (e.g., 2-aminoethyl, 2-amino-1-(aminomethyl)ethyl) is bound to the terminal carboxyl group via ester linkage, (ii) lactic acid-glycolic acid copolymers wherein an L-amino acid compound having a hydroxyl group derivatized by reduction of the carboxyl group (e.g., L-alaninol, L-lysinol, L-arginol) is bound to the terminal carboxyl group via ester linkage, (iii) lactic acid-glycolic acid copolymers wherein an L-α-amino acid (e.g., L-glycine, L-alanine, L-lysine, L-arginine), a β-amino acid (e.g., β-aminopropionic acid, β-guanidinobutanoic acid) or a γ-amino acid (e.g., γ-aminobutanoic acid, γ-guanidinobutanoic acid) is bound to the terminal hydroxyl group, and lactic acid-glycolic acid copolymers consisting of combinations thereof and having a basic group at both terminals.

Examples of the bioactive substances having an acidic group, comprised in the sustained-release preparation of the present invention, include bioactive substances having a free group such as a sulfone group, a carboxyl group, a phosphoric acid group or a hydroxamic acid group, or salts thereof.

The salt of the bioactive substance of the present invention is preferably a pharmaceutically acceptable salt. Such pharmaceutically acceptable salts include salts with inorganic bases, salts with organic bases and salts with basic or acidic amino acids. Inorganic bases capable of forming such salts include alkali metals (e.g., sodium, potassium) and alkaline earth metals (e.g., calcium, magnesium), such organic bases include trimethylamine, triethylamine, pyridine, picoline, N,N-dibenzylethylenediamine and diethanolamine, such inorganic acids include hydrochloric acid, hydrobromic acid, hydroiodic acid, phosphoric acid, nitric acid and sulfuric acid, such organic acids include formic acid, acetic acid, trifluoroacetic acid, oxalic acid, tartaric acid, fumaric acid, maleic acid, methanesulfonic acid, benzenesulfonic acid, p-toluenesulfonic acid and citric acid, and such basic or acidic amino acids include arginine, lysine, aspartic acid and glutamic acid. The salt is preferably be acidic.

The bioactive substance is not subject to limitation as to pharmacological effect; useful medicaments to which such bioactive substances are applied include the medicaments for treating or preventing diseases or symptoms such as psychotropic disease (e.g., Alzheimer's disease, senile dementia, cerebral infarction, transient cerebral ischemic attack), pain, circulatory diseases (e.g., hypertension, thrombosis, heart failure, ischemic heart disease, myocardial infarction, for angina pectoris, peripheral circulatory disorder), bone/joint diseases (e.g., osteoporosis, rheumatoid arthritis), infections (e.g., bacterial infections, viral infections, AIDS, hepatitis B, hepatitis C, or herpes zoster), diabetes mellitus, atherosclerosis, hyperlipidemia, allergic diseases (e.g., asthma, atopic dermatitis), gastrointestinal disease (e.g., gastric ulcer, duodenal ulcer, pancreatitis) and cancer (e.g., prostatic cancer, breast cancer).

In addition to the bioactive substances, the a sustained-release preparation comprising it may comprise other additives, e.g., dispersing agents (surfactants such as Tween 80 and HCO-60; polysaccharides such as carboxymethyl cellulose, sodium alginate and sodium hyaluronate; protamine sulfate; polyethylene glycol 400 etc.), preservatives (e.g., methyl paraben, propyl paraben), isotonizing agents (e.g., sodium chloride, mannitol, sorbitol, glucose), oils and fats (e.g., sesame oil, corn oil), phospholipids (e.g., lecithin), excipients (e.g., lactose, corn starch, mannitol, cellulose), binders (e.g., sucrose, gum arabic, methyl cellulose, carboxymethyl cellulose, dextrin) and disintegrants (e.g., carboxymethyl cellulose calcium).

Examples of production methods for a biodegradable polymer having an optionally protected basic group for the present invention include, but are not limited to, the methods described below.

A biodegradable polymer having an optionally protected basic group for the present invention can be produced by subjecting a compound having an optionally protected basic group and a cyclic ester compound to a ring-opening polymerization and/or ester exchange reaction.

Specifically, by subjecting cyclic ester compound [I], which has a protected basic group and a functional group with active hydrogen (e.g., hydroxyl group, thiol group, amino group, imino group), and a cyclic ester compound to a ring-opening polymerization and/or ester exchange reaction using an ester exchange catalyst, biodegradable polymer [II], wherein the protected basic group is introduced to the carboxyl terminal via ester, thioester or amide linkage, is obtained.

The cyclic ester compound means, for example, a cyclic compound having at least 1 ester linkage within the ring thereof. Specifically, such compounds include lactones (e.g., β-propiolactone, δ-valerolactone, ε-caprolactone), lactides (e.g., glycolide, L-lactide, D-lactide, DL-lactide, meso-lactide) and morpholine-2,5-dione, two or more kinds of which may be used concurrently.

The ester exchange catalyst is exemplified by organic tin catalysts (e.g., tin octoate, di-n-butyltin dilaurate, tetraphenyltin) and aluminum catalysts (e.g., triethylaluminum) and zinc catalysts (e.g., diethyl zinc).

Polymerization can be achieved by the bulk polymerization method, in which the reaction is carried out with the reaction mixture in a melted state, and the solution polymerization method, in which the reaction is carried out with the reaction mixture dissolved in an appropriate solvent (e.g., benzene, toluene, decalin, dimethylformamide). Although polymerization temperature is not subject to limitation, it exceeds the temperature at which the reaction mixture is melted at reaction initiation, normally 100 to 300° C., for bulk polymerization, and is normally room temperature to 100° C. for solution polymerization. If the reaction temperature exceeds the boiling point of the reaction solution, refluxing with a condenser can be used, or the reaction can be carried out in a pressure-resistant container. Polymerization time is determined as appropriate, in consideration of polymerization temperature and other reaction conditions, the physical properties of the desired polymer, etc., from 10 minutes to 72 hours, for example. After completion of the reaction, the reaction mixture may be dissolved in an appropriate solvent (e.g., acetone, dichloromethane, chloroform) as necessary, and after polymerization is stopped with an acid (e.g., hydrochlorid, acetic anhydride), the desired product may be precipitated and isolated by, for example, mixing the solution in a solvent that does not dissolve the desired product (e.g., methanol, ethanol, water, ether). Polymer [II] is then subjected to a deprotection reaction suitable for the protecting group to yield polymer [III], wherein a basic group is introduced to the carboxyl terminal of the starting polymer via ester, thioester or amide linkage. By derivatizing a carboxylic acid having a protected basic group to an active acyl derivative (e.g., acid anhydride, acid chloride) [IV], and reacting with the hydroxyl terminal of polymer [II], polymer [V], which has a protected basic group at each end of the polymer, is obtained. Alternatively, the hydroxyl terminal of a polymer synthesized by a known method (e.g., catalyst-free condensation polymerization via dehydration) is reacted with active acyl derivative [IV] to yield polymer [VI], which has a protected basic group at the hydroxyl terminal. The terminal carboxyl group of polymer [VI] is then activated by a known method and reacted with compound [I] to yield polymer [V], which has a protected basic group at each terminal. polymer [V] is then subjected to a deprotection reaction suitable for the protecting group to yield polymer [VII], which has a basic group at each terminal.

By homo-polymerizing a cyclic compound having a protected basic group outside the ring thereof or by copolymerizing a cyclic ester compound not containing a basic group (e.g., glycolide, lactide, ε-caprolactone), and subsequently deprotecting the compound by a known method, a polymer compound having an amino group on a side chain thereof can be synthesized.

An example of the above-described production process is given below but not to be construed as limitative.

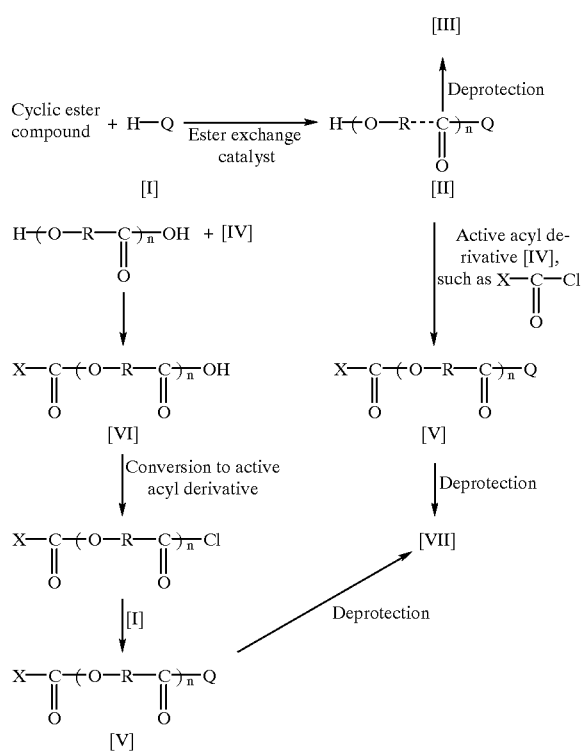

In the above reaction scheme, Q represents

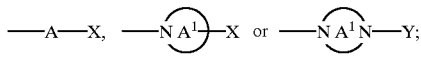

R represents divalent hydrocarbon group.

The A, $A^1$, $A^2$, X and Y have the same definitions as those shown above. The divalent hydrocarbon group represented by R is a group resulting from elimination of 1 hydrogen atom from the above-described hydrocarbon group, and may have an amide linkage therein. Examples of hydrocarbons containing an amide linkage therein include —$CH_2$—CONH—$CH_2$—.

The biodegradable polymer of the present invention can be produced by subjecting a compound having an optionally protected basic group [I] and a biodegradable polymer [VIII] produced by the known method (e.g., catalyst-free condensation polymetrization via dehydration). Specifically, by subjecting the compound [I] and the biodegradable polymer [VIII] to a condensation reaction using a dehydrating agent and/or activator of the functional group according to the necessity.

The functional group such as amino group or carboxyl group which reacts in the condensation reaction can be activated by a known manner. Examples of the activating manner include such as forming an active ester (e.g., ester with a substituted phenols (e.g., pentachlorophenol; 2,4,5-trichlorophenol, 2,4-dinitrophenol, p-nitrophenol) or N-substituted imides (e.g., N-hydroxy-5-norbornene-2,3-dicarboximide, N-hydroxysuccinimide, N-hydroxy-1,2,3-benzotriazol)), carboxylic anhydride or azide with carboxylic acid of the starting material, acyl chloride method, oxidation-reduction method, N,N'-dicyclohexylcarbodimide N,N'-dicyclohexylcarbodimide-additives method, a method using Woodward reagent K, a method using benzotriazol-1-yl-oxy-tris(dimethylamino)-phosphonium hexafuluorophosphate (BOP reagent) or the like.

The condensation reaction is generally carried out in the solvent which do not prevent the reaction. The example of the solvent includes (amides such as dimethyl formamide, ethers such as tetrahydrofuran or dioxane, halogenate hydrocarbons such as dichloromethane or chloroform, alcohol such as ethanol or methanol N-methylpyrrolidone, N-methylmorpholine, water or the like. The reaction temaperature is preferably in a range of about −30° C. to about 50° C. The reaction temperature is more preferably about 0° C. to about 40° C. The reaction period is about 10 minutes to about 24 hours.

When the resulting polymer of the above condensation reaction has a protective group, the deprotection reaction is carried out according to per se known method. Such method is not limited as long as it can remove the protecting group without influence on ester linkage or amide linkage of the polymer. Examples of the method include such as oxidation, reduction, acid treatment or the like.

Reduction includes catalytic reduction using a catalyst (e.g., palladium-carbon, palladium-black, platinum-oxide), reduction with sodium in liquid ammonium, reduction with dithiothreitol or the like.

Acid treatment includes, for example, acid treatment with an inorganic acid inorganic acid (e.g., hydrogen fluoride, hydrogen bromide, hydrogen chloride) or organic acid (e.g., trifluoroacetic acid, methansulfonic acid, trifluoromethansulfonic acid) or mixture thereof. Suitable cation scavenger (e.g., anisole, phenol, thioanisole, is preferably add to the reaction solution on the acid treatment.

The biodegradable polymer thus obtained can be used as a base for production of a sustained-release preparation.

The ratio by weight of the bioactive substance to the base of the present invention is normally about 0.001 to about 40% (w/w), preferably about 0.02 to about 30% (w/w), and more preferably about 0.1 to 20% (w/w) for a polypeptide, and normally about 0.01 to 80% (w/w), preferably about 0.1 to 50% (w/w) for a non-peptide substance.

A sustained-release preparation of the present invention is produced by, for example, the in-water drying method, the phase separation method, the spray drying method or a method based thereof. Production methods for a sustained-release preparation, e.g., a microcapsule preparation, are hereinafter described. The term "microcapsule" used herein is intend to include microsphere, microcapsules and microparticles.

(1) In-Water Drying Method (o/w Method)

In this method, an organic solvent solution of a bioactive substance is first prepared. The organic solvent used to produce the sustained-release preparation of the present invention preferably has a boiling point of not higher than 120° C. The organic solvent is exemplified by halogenated hydrocarbons (e.g., dichloromethane, chloroform, carbon tetrachloride), alcohols (e.g., ethanol, methanol), acetonitrile and acetone, with preference given to dichloromethane, acetonitrile etc., dichloromethane being most desirably used. These solvents may be used as a mixture in an appropriate ratio. Although the biodegradable polymer concentration in the organic solvent solution varies depending on the molecular weight of the biodegradable polymer, the kind of organic solvent etc., it is normally chosen over the range from about 0.01 to about 80% (w/w), preferably about 0.1 to about 70% (w/w), concentrations of about 1 to about 60% being most desirably used.

The bioactive substance is added to, and dissolved in, the thus-prepared organic solvent solution of the biodegradable polymer. The amount of bioactive substance added is set so that the upper limit of the bioactive substance: biodegradable polymer ratio by weight is up to about 1:2, preferably up to about 1:3.

The organic solvent solution thus prepared is then added to an aqueous phase, followed by the formation of an o/w emulsion using a turbine type mechanical stirrer or the like, after which the oil phase solvent is evaporated to yield microcapsules. The volume of aqueous phase is normally chosen over the range from about 1 time to about 10,000 times, preferably about 2 times to about 5,000 times, the volume of oil phase. Most preferably, the volume of aqueous phase is chosen over the range from about 5 times to about 2,000 times.

An emulsifier may be added to the above-described external aqueous phase. The emulsifier is normally not subject to limitation, as long as it is capable of forming a stable o/w emulsion. Examples of such emulsifiers include anionic surfactants (e.g., fatty acid soaps, N-acylamino acids, alkyl ether carboxylates, acylated peptides, alkylbenzenesulfonates, alkylnaphthalenesulfonates, naphthalenesulfonate-formalin polymerization condensates, melaminesulfonate-formalin polymerization condensates, dialkylsulfosuccinic ester salts, alkylsulfoacetates, α-olefinsulfonates, N-acylmethyltaurine, sulfated oil, higher alcohol sulfuric ester salts, secondary higher alcohol sulfuric ester salts, alkylether sulfates, secondary higher alcohol ethoxysulfates, polyoxyethylene alkylphenyl ether sulfates, monoglysulfates, fatty acid alkylolamide sulfuric ester salts, alkyl ether phosphoric ester salts, alkylphosphoric ester salts), nonionic surfactants (e.g., polyoxyethylene alkyl ethers, single chain length polyoxyethylene alkyl ethers, polyoxyethylene secondary alcohol ethers, polyoxyethylene alkylphenyl ethers, polyoxyethylene sterol ethers, polyoxyethylene lanoline derivatives, ethylene oxide derivatives of alkylphenol-formalin condensates, polyoxyethylene polyoxypropylene block polymers, polyoxyethylene polyoxypropylene alkyl ethers, polyoxyethylene glycerol fatty acid esters, polyoxyethylene sorbitan fatty acid esters, polyoxyethylene sorbitol fatty acid esters, polyethyleneglycol fatty acid esters, fatty acid monoglycerides, polyglycerol fatty acid esters, sorbitan fatty acid esters, propyleneglycol fatty acid esters, sucrose fatty acid esters, fatty acid alkanolamides, polyoxyethylene fatty acid amides, polyoxyethylene alkylamines, alkylamine oxides), polyoxyethylene castor oil derivatives (e.g., polyoxyethylene hardened castor oils 5, 10, 20, 40, 50, 60, 100 E.O., polyoxyethylene castor oil), polyvinylpyrrolidone, polyvinyl alcohol, carboxymethyl cellulose, lecithin, gelatin and hyaluronic acid. These may be used in combination as appropriate. The emulsifier concentration in the external aqueous phase is, for example, about 0.001% to about 20% (w/w), preferably about 0.01% to about 10% (w/w), concentrations of about 0.05% to about 5% (w/w) being desirably used.

In the above-described o/w method, the method in which a bioactive substance is dispersed in an organic solvent solution of a biodegradable polymer, i.e., the s/o/w method, may be used to produce microcapsules.

(2) In-water Drying Method (w/o/w Method)

In this method, an organic solvent solution of a bioactive substance is first prepared. The organic solvent used is identical to that described above. Although the biodegradable polymer concentration in the organic solvent solution varies depending on the molecular weight of the biodegradable polymer, the kind of organic solvent etc., it is normally chosen over the range from about 0.01 to about 80% (w/w). Preferably, it is chosen over the range from about 0.1 to about 70% (w/w), concentrations of about 1 to about 60% being most desirably used. As an internal aqueous phase, an aqueous dispersion of a bioactive substance is used. The bioactive substance concentration in the aqueous dispersion is, for example, about 10% (w/v) to about 90% (w/v). The above-described aqueous dispersion of the bioactive substance is emulsified and dispersed in the organic solvent solution of the biodegradable polymer to yield a w/o emulsion. This emulsification is achieved by a known method of dispersion, using, for example, a turbine type mechanical stirrer, a homogenizer, or the like. The upper limit of the ratio by weight of the internal aqueous phase and the biodegradable polymer is set at up to about 1:2, preferably up to about 1:3. The ratio of the internal aqueous phase and the organic solvent solution of the biodegradable polymer is normally 1:1,000 (v/v) to 1:1 (v/v), preferably 1:100 (v/v) to 1:5 (v/v), and most preferably 1:50 (v/v) to 1:5 (v/v).

The w/o emulsion thus produced is then added to another aqueous phase to yield a w/o/w emulsion, followed by evaporation of the oil phase solvent, to yield microcapsules. The specific operation is the same as that described in term (1) above.

The sustained-release preparation of the present invention can be administered as such in the form of the microcapsules obtained above, or in the form of various dosage forms prepared from the microcapsules as such or a spherical, needle, pellet, film or cream pharmaceutical composition as a starting material. The dosage form is exemplified by non-oral preparations (e.g., intramuscular, subcutaneous, visceral or other injectable or indwellable preparations; nasal, rectal, uterine or other transmucosal preparations) and oral preparations (e.g., hard capsules, soft capsules, granules, powders, suspensions).

The bioactive substance content in the sustained-release preparation of the present invention is normally about 0.001 to about 40% (w/w), preferably about 0.02 to about 30% (w/w), and more preferably about 0.1 to about 20% (w/w) for a polypeptide, and about 0.01 to about 80% (w/w), preferably about 0.1 to about 50% (w/w) for a non-peptide substance.

An injectable sustained-release preparation of the present invention can be prepared by suspending microcapsules obtained by one of the above-described methods in water, along with a dispersing agent (e.g., surfactants such as Tween 80 and HCO-60; polysaccharides such as carboxymethyl cellulose, sodium alginate and sodium hyaluronate; protamine sulfate, polyethylene glycol 400), a preservative (e.g., methyl paraben, propyl paraben), an isotonizing agent (e.g., sodium chloride, mannitol, sorbitol, glucose), a local anesthetizing agent (e.g., xylocaine hydrochloride, chlorobutanol) etc., to yield an aqueous suspension, or by dispersing it in a vegetable oil (e.g., sesame oil, corn oil) with or without a phospholipid (e.g., lecithin) or a moderate-chain fatty acid triglyceride (e.g., MIGLYOL 812), to yield an oily suspension.

When the sustained-release preparation of the present invention is a microcapsule, its average particle diameter is normally about 0.1 to about 300 μm, preferably about 1 to about 150 μm, and more preferably about 2 to about 100 μm.

The above-described microcapsule can be prepared as a sterile preparation without limitation by, for example, the method in which the entire production process is sterile, the method in which gamma rays are used as sterilant, and the method in which an antiseptic is added.

The sustained-release preparation of the present invention can be safely used in mammals (e.g., humans, bovines, swines, dogs, cats, mice, rats, rabbits).

Prophylactic or therapeutic indications for sustained-release preparations of the present invention vary according to the bioactive substance used. For example, sustained-release preparations of the present invention are used as medicaments for preventing or treating diseases or symptoms such as psychotropic disease (e.g., Alzheimer's disease, senile dementia, cerebral infarction, transient cerebral ischemic attack), pain, circulatory diseases (e.g., hypertension, thrombosis, heart failure, ischemic heart disease, myocardial infarction, angina pectoris, peripheral circulatory disorder), bone/joint diseases (e.g., osteoporosis, rheumatoid arthritis), infections (e.g., bacterial infections, viral infections, AIDS, hepatitis B, hepatitis C, or herpes zoster), diabetes mellitus, atherosclerosis, hyperlipidemia, allergic diseases (e.g., asthma, atopic dermatitis), gastrointestinal disease (e.g., gastric ulcer, duodenal ulcer, pancreatitis) and cancer (e.g., prostatic cancer, therapeutic drugs for breast cancer).

Depending on the type and content of the bioactive substance, duration of release, target disease, subject animal, sex, age and other factors, the dose of the sustained-release preparation of the present invention may be set at any level, as long as an effective concentration of the bioactive substance is retained in the body. The dose of the preparation of the present invention may be such that a commonly known effective amount of a bioactive substance is administered; for example, the dose may be chosen as appropriate over the range from about 0.0001 to about 100 mg/kg body weight, based on the bioactive substance, for each adult. When the bioactive substance used is the endothelin antagonist cyclo [D-α-aspartyl-3-[(4-phenylpiperazin-1-yl)carbonyl]-L-alanyl-L-α-aspartyl-D-2-(2-thienyl)glycyl-L-leucyl-D-tryptophyl] disodium salt, and when it is administered by injection to an adult patient with hypertension, it is used at about 1 mg/kg to about 20 mg/kg body weight as an active ingredient dose per administration. Dosing frequency may be chosen as appropriate, e.g., once every 1 to 3 days or every 1 week to 3 months, depending on various factors.

Owing to the use of biodegradable polymer having a basic group as a base the sustained-release preparation of the present invention provides various effects, including improved entrapment ratio for bioactive substances having an acidic group, suppressed drug leakage early after administration, and constant sustained release for an extended period of time. Thus, the biodegradable polymer having a basic group is quite useful as a base for sustained-release preparations of acidic agents.

EXAMPLES

The present invention is hereinafter described in more detail by means of the following working examples and experimental examples, which are not to be construed as limitative.

Example 1

After 0.6 ml of ethyl acetate was added to 0.5114 g of benzyl N-(2-hydroxyethyl)carbamate (produced by Tokyo Kasei, Japan) and dissolved at 40° C., the solution was kept standing at room temperature. The precipitated crystal was collected by filtration through a 0.5 μm PTFE filter, washed with n-hexane, and dried overnight under reduced pressure in the presence of diphosphorus pentaoxide.

This crystal, 117.5 mg, was placed in a 50 ml three-mouthed flask and molten at 60 to 64° C. in dry nitrogen; 450 μl of a 15% toluene solution of triethylaluminum was added, immediately followed by the addition of 867.9 mg of L-lactide; the flask was sealed and immersed in oil to the extent that its inner empty space was totally covered with the oil, followed by heating to 110° C. and polymerization for 4 hours. After completion of the reaction, the reaction product was dissolved in 10 ml of chloroform, followed by the addition of 1 ml of hydrogen chloride/methanol and stirring for 5 hours. This solution was filtered through a 0.2 am PTFE filter, then concentrated under reduced pressure, after which it was added drop by drop to 50 ml of methanol under stirring conditions. Stirring was continued overnight. The precipitated polymer was centrifuged (20,000 rpm, 10° C., 30 minutes). This polymer was washed with methanol, then with diethyl ether, and dried under reduced pressure to yield a white powder of a poly(L-lactide) wherein 2-(N-benzyloxycarbonyl)aminoethanol was bound to the terminal carboxyl group via ester linkage.

As determined by GPC, number-average molecular weight (hereinafter symply abbreviates Mn)=4,400 and weight-average molecular weight (hereinafter symply abbreviate as MW)=6,000; $^1$H-NMR (CDCl$_3$) of the polymer demonstrated poly(L-lactide) signals of δ=1.58 ppm (doublet, CH$_3$) and 5.17 ppm (quartet, CH) and a phenyl signal of δ=7.34–7.35 ppm.

Example 2

A commercial product of tin octoate was used after distillation under reduced pressure (169° C., 2.7 mmHg). To a 50 ml three-mouthed flask, 1.2316 g of L-lactide and 0.3336 g of benzyl N-(2-hydroxyethyl)carbamate were added, followed by heating to 100° C. for melting. In dry nitrogen, 50 μl of tin octoate was added, followed by polymerization at 140° C. for 4 hours. After completion of the reaction, the reaction product was dissolved in 2 ml of chloroform and added drop by drop to 20 ml of methanol under stirring conditions. The polymer was recovered by centrifugation (20,000 rpm, 10° C., 30 minutes), again dissolved in 2 ml of chloroform, and filtered through a 0.2 μm PTFE filter, after which the filtrate was added drop by drop to 20 ml of methanol. The precipitated polymer was centrifugally recovered, washed with diethyl ether, and dried under reduced pressure to yield a white powder of a poly (L-lactide) wherein 2-(N-benzyloxycarbonyl)aminoethanol was bound to the terminal carboxyl group via ester linkage.

As determined by GPC, Mn=3,700 and Mw=4,500; $^1$H-NMR (CDCl$_3$) of the polymer demonstrated poly(L-lactide) signals of δ=1.58 ppm (doublet, CH$_3$) and 5.17 ppm (quartet, CH) and a phenyl signal of δ=7.35 ppm. The number-average molecular weight determined from the ratio of their peak areas on the basis of the terminal group quantitation method was Mn=2,800.

Example 3

To a 50 ml three-mouthed flask, 6.0106 g of DL-lactide and 195.55 mg of 2-(N-benzyloxycarbonyl)aminoethanol were added, followed by heating to 125° C. for melting. In dry nitrogen, 50 μl of tin octoate was added, followed by polymerization at 150° C. for 3 hours. After completion of the reaction, 5 ml of chloroform was added to the reaction product, followed by overnight shaking to dissolve the reaction product, after which the resulting solution was added drop by drop to 100 ml of methanol under stirring conditions. The polymer was recovered by centrifugation (4,800 rpm, 5° C., 20 minutes) and purified by re-precipitation with acetone/ethanol. The polymer recovered by re-centrifugation was dissolved in 3 ml of dioxane, after which it was freeze-dried to yield a poly(DL-lactide)

wherein 2-(N-benzyloxycarbonyl)aminoethanol was bound to the terminal carboxyl group via ester linkage.

As determined by GPC, Mn=8,200 and Mw=14,100; the number-average molecular weight determined from $^1$H-NMR (CDCl$_3$) of the polymer on the basis of the terminal group quantitation method was Mn=10,500.

Example 4

To a 50 ml three-mouthed flask, 7.7760 g of DL-lactide and 126.81 mg of 2-(N-benzyloxycarbonyl)aminoethanol were added, followed by heating to 125° C. for melting. In dry nitrogen, 50 µl of tin octoate was added, followed by polymerization at 150° C. for 3 hours. After completion of the reaction, 5 ml of acetone was added to the reaction product, followed by overnight shaking to dissolve the reaction product, after which the resulting solution was added drop by drop to 320 ml of ethanol under stirring conditions. The precipitate obtained by discarding the supernatant by decantation was purified by re-precipitation with acetone/ethanol. This precipitate was dissolved in dioxane and freeze-dried to yield a poly(DL-lactide) wherein 2-(N-benzyloxycarbonyl)aminoethanol was bound to the terminal carboxyl group via ester linkage. As determined by GPC, Mn=9,100 and Mw=21,100.

Example 5

233.7 mg of the polymer obtained in Example 3 was dissolved in 20 ml of ethyl acetate; while this solution was vigorously stirred using a magnetic stirrer, nitrogen bubbling was first conducted for 10 minutes, followed by the addition of 128 mg of palladium-carbon (5%), after which bubbling was continued for 10 more minutes. Nitrogen bubbling was then switched to hydrogen bubbling; the reaction was carried out at room temperature for 6.5 hours. The residual hydrogen was then purged from the reactor using nitrogen; the reaction solution was filtered through a 0.1 µm PTFE filter to remove the catalyst. This filtrate was concentrated and dried under reduced pressure to yield a poly(DL-lactide) wherein 2-aminoethanol was bound to the terminal carboxyl group via ester linkage.

As determined by GPC, Mn=8,000 and Mw=15,000. The completion of benzyloxycarbonyl group dissociation was confirmed by the disappearance of the 7.35 ppm signal in $^1$H-NMR (CDCl$_3$) of the resulting polymer. Also, a chloroform solution of the resulting polymer was spotted onto a Kieselgel 60 silica gel plate using a capillary tube, and dried. After a 0.5% n-butanol solution of ninhydrin was sprayed, the plate was heated using a drier. A color developed, demonstrating the presence of the amino group.

Example 6

247.5 mg of the polymer obtained in Example 2 was dissolved in 20 ml of ethyl acetate; while this solution was vigorously stirred using a magnetic stirrer, nitrogen bubbling was first conducted for 10 minutes, followed by the addition of 140.3 mg of palladium-carbon (5%), after which bubbling was continued for 10 more minutes. Nitrogen bubbling was then switched to hydrogen bubbling; the reaction was carried out at room temperature for 8.5 hours. The residual hydrogen was then purged from the reactor using nitrogen; the reaction solution was filtered through a 0.1 µm PTFE filter to remove the catalyst. This filtrate was concentrated and dried under reduced pressure to yield a poly(L-lactide) wherein 2-aminoethanol was bound to the terminal carboxyl group via ester linkage.

As determined by GPC, Mn=3,200 and Mw=4,100. The completion of benzyloxycarbonyl group dissociation was confirmed by the disappearance of the 7.35 ppm signal in $^1$H-NMR (CDCl$_3$) of the resulting polymer. Also, a chloroform solution of the resulting polymer was spotted onto a Kieselgel 60 silica gel plate using a capillary tube, and dried. After a 0.5% n-butanol solution of ninhydrin was sprayed, the plate was heated using a drier. A color developed, demonstrating the presence of the amino group.

Example 7

To a 50 ml three-mouthed flask, 12.2207 g of DL-lactide and 477.1 mg of 2-(N-benzyloxycarbonyl)aminoethanol were added, followed by heating to 125° C. until melting. In dry nitrogen, 70 µl of tin octoate was added, followed by polymerization at 150° C. for 3 hours. After completion of the reaction, 10 ml of acetone was added to the reaction product, followed by overnight shaking to dissolve the reaction product, after which the resulting solution was added drop by drop to 400 ml of cold ethanol under stirring conditions. The precipitate obtained by discarding the supernatant by decantation was purified by re-precipitation with acetone/ethanol. A portion of the precipitate was dried under reduced pressure and subjected to GPC and $^1$H-NMR (CDCl$_3$). As determined by GPC, Mn=6,300 and Mw=11,600.

The number-average molecular weight determined from $^1$H-NMR (CDCl$_3$) of the polymer on the basis of the terminal group quantitation method was Mn=7,700.

All remaining precipitate was dissolved in 20 ml of ethyl acetate and reacted in the presence of 2.5417 g of palladium-carbon for 8 hours, in accordance with the method of Example 5 to yield a poly(DL-lactide) wherein 2-aminoethanol was bound to the terminal carboxyl group via ester linkage.

As determined by GPC, Mn=5,800 and Mw=11,900. The completion of benzyloxycarbonyl group dissociation was confirmed by the disappearance of the 7.35 ppm signal in $^1$H-NMR (CDCl$_3$) of the resulting polymer. Also, a chloroform solution of the resulting polymer was spotted onto a Kieselgel 60 silica gel plate using a capillary tube, and dried. After a 0.5% n-butanol solution of ninhydrin was sprayed, the plate was heated using a drier. A color developed, demonstrating the presence of the amino group.

Example 8

After 0.5090 g of 2-(N-benzyloxycarbonyl)aminoethanol was placed in a 50 ml three-mouthed flask and molten at 75° C. in dry nitrogen; 2 ml of a 15% toluene solution of triethylaluminum was added. Subsequently, 5.2160 g of L-lactide was immediately added; the flask was tightly stoppered and immersed in oil to the extent that the flask's inner empty space was totally covered with the oil, followed by heating to 150° C. and polymerization for 30 minutes. After completion of the reaction, the reaction product was dissolved in 10 ml of chloroform (solution A). To a 2 ml portion of this solution, hydrogen chloride/methanol was added, followed by stirring for 5 hours. This solution was purified by two times of re-precipitation with chloroform/ethanol to yield a poly(L-lactide) wherein 2-(N-benzyloxycarbonyl)aminoethanol was bound to the terminal carboxyl group via ester linkage.

As determined by GPC, Mn=5,200 and Mw=7,300. The number-average molecular weight determined from $^1$H-NMR (CDCl$_3$) of the polymer on the basis of the terminal group quantitation method was Mn=8,500.

Example 9

To a 2 ml portion of solution A of Example 8, 4 ml of chloroform was added; to this dilution, 1 ml of acetic anhydride was added, followed by refluxing or 6.5 hours. After being concentrated, the reaction mixture was purified by three times of re-precipitation with chloroform/ethanol to yield a poly(L-lactide) wherein the hydroxyl terminal was acetylated and wherein 2-(N-benzyloxycarbonyl) aminoethanol was bound to the terminal carboxyl group via ester linkage.

As determined by GPC, Mn=5,500 and Mw=7,800. $^1$H-NMR (CDCl$_3$) of the polymer demonstrated poly(L-lactide) signals of δ=1.58 ppm (doublet, CH$_3$) and 5.17 ppm (quartet, CH) and a phenyl signal of δ=7.35 ppm, as well as a terminal acetyl methyl proton signal of δ=2.13 ppm (singlet). The number-average molecular weight determined from the $^1$H-NMR (CDCl$_3$) of the polymer on the basis of the terminal group quantitation method was M=7,600.

Example 10

1.0642 g of 2-(N-benzyloxycarbonyl)aminoethanol, 23.7392 g of DL-lactide and 6.2648 g of glycolide were placed in a three-mouthed flask and molten at 125° C. To this mixture, 50 μl of tin octoate was added in dry nitrogen; the flask was sealed and immersed in oil to the extent that the flask's inner empty space was totally covered with the oil, followed by heating to 150° C. and polymerization for 3 hours. After completion of the reaction, the reaction product was dissolved in 34 ml of acetone; this solution was mixed in 1,500 ml of ethanol under stirring conditions to precipitate the polymer. The supernatant was removed by decantation; 30 ml of acetone was added to dissolve the precipitate. This solution was again mixed in 1,500 ml of ethanol under stirring conditions. The polymer recovered was dried under reduced pressure.

As determined by GPC, Mn=6,500 and Mw=14,500. $^1$H-NMR (CDCl$_3$) of the polymer demonstrated L/G (mole ratio)=75.3/24.7. The number-average molecular weight determined on the basis of the terminal group quantitation method was Mn=7,100.

Example 11

2 mg of phenol red (produced by Wako Pure Chemical Industry, Japan) was suspended in 0.05 ml of water; this suspension was added to a solution of 1 g of the polymer obtained in Example 7, which contained a basic group, in 1.2 ml of dichloromethane, followed by mixing using a small homogenizer (Polytron, produced by Kinematica, Switzerland) for 60 seconds, to yield a w/o emulsion. This emulsion was injected to 400 ml of a 0.1% (w/v) aqueous solution of polyvinyl alcohol (Gosenol EG-40, produced by The Nippon Synthetic Chemical Industry, Japan), followed by stirring at 7,000 rpm using a small homogenizer (Autohomomixer, produced by TOKUSHU KIKA, Japan), to yield a w/o/w emulsion. While the w/o/w emulsion was stirred at room temperature for 3 hours, the internal w/o emulsion was then solidified by dichloromethane volatilization, after which this suspension was sieved through a 125 μm mesh sieve, then collected using a centrifuge. This was again dispersed in water and re-centrifuged; the drug released was washed away.

The microcapsules collected were freeze-dried to ensure solvent removal and dehydration and yield a powder (lot No. A).

For comparison, microcapsules (lot No. B) were prepared by the same method as that described above but the polymer was replaced with a polylactide (PLA) having a weight-average molecular weight of 12,000 (produced by Wako Pure Chemical Industry).

Experimental Example 1

(Release Test)

Each microcapsule preparation, 20 mg, was weighed into a 10 ml vial; 10 ml of Dulbecco's phosphate buffer (Ca/Mg-free, produced by Wako Pure Chemical Industry) containing 0.05% (w/v) Tween 80 (produced by Wako Pure Chemical Industry) was added; the vial was sealed. This vial was shaken at 37° C. and 120 spm; after a given period of time, this suspension was filtered; the drug was quantified from the ultraviolet absorption of the filtrate at 558 nm.

The percent ratios (entrapment ratio) of the contents achieved to the contents charged for both microcapsule preparations, and the percent ratios (retention rates) of the drug contents in the microcapsule after 1 day of release test to the initial contents are shown in Table 1.

TABLE 1

| Lot No. | Entrapment Ratio (%)[a] | 1-day Retention Rate (%)[a] |
|---------|-------------------------|------------------------------|
| A       | 100.3 ± 2.4             | 94.0 ± 0.4                   |
| B       | 77.1 ± 2.4              | 53.7 ± 0.8                   |

[a] n = 3

As shown in Table 1, the microcapsule of the present invention almost completely trapped phenol red, which contains the sulfone group, and the initial burst of the microcapsule of the present invention was dramatically smaller than that of the microcapsule incorporating a PLA having a terminal carboxyl group, demonstrating the excellency of the microcapsule of the present invention as a base for sustained-release preparation.

Example 12

200 mg of the endothelin antagonist cyclo[D-α-aspartyl-3-[(4-phenylpiperazin-1-yl)carbonyl]-L-alanyl-L-α-aspartyl-D-2-(2-thienyl)glycyl-L-leucyl-D-tryptophyl] disodium salt (compound A) was suspended in 0.2 ml of water; this suspension was added to a solution of 1.8 g of the polymer obtained in Example 7, which contained a basic group, in 2 ml of dichloromethane, followed by mixing using a small homogenizer (Polytron, produced by Kinematica) for 60 seconds, to yield a w/o emulsion. This emulsion was injected to 400 ml of a 0.1% (v/w) aqueous solution of polyvinyl alcohol (Gosenol EG-40, produced by The Nippon Synthetic Chemical Industry, Japan), followed by stirring at 7,000 rpm using a small homogenizer (Autohomomixer, produced by TOKUSHU KIKA), to yield a w/o/w emulsion. While the w/o/w emulsion was stirred at room temperature for 3 hours, the internal w/o emulsion was then solidified by dichloromethane volatilization, after which this suspension was sieved through a 125 μm mesh sieve, then collected using a centrifuge. This was again dispersed in water and re-centrifuged; the drug released was washed away.

The microcapsules collected were freeze-dried to ensure solvent removal and dehydration and yield a powder (lot No. C).

For comparison, microcapsules (lot No. D) were prepared by the same method as that described above but the polymer was replaced with a PLA having a molecular weight of 12,000.

Experimental Example 2

(Release Test)

Each microcapsule preparation, 20 mg, was weighed into a 10 ml vial; 10 ml of Dulbecco's phosphate buffer (Ca/

Mg-free, produced by Wako Pure Chemical Industry) containing 0.05% (w/v) Tween 80 (produced by Wako Pure Chemical Industry, Japan) was added; the vial was tightly stoppered. This vial was shaken at 37° C. and 120 spm; after a given period of time, a portion of this suspension was filtered; compound A was quantified by HPLC of the filtrate.

The percent ratios (entrapment ratio) of the compound A contents achieved to the contents charged for both microcapsule preparations, and the percent ratios (retention rates) of the drug contents in the microcapsule after 1 day of release test to the initial contents are shown in Table 2.

TABLE 2

| Lot No. | Entrapment Ratio (%)[a] | 1-day Retention Rate (%)[a] |
|---|---|---|
| C | 85.3 ± 0.4 | 99.2 ± 0.0 |
| D | 88.7 ± 1.0 | 32.5 ± 4.8 |

[a] n = 3

As shown in Table 2, the microcapsule of the present invention almost completely suppressed initial burst.

The changes over time in retention rate during a 4-week period with the same experimental system are shown in Table 3.

TABLE 3

| Time | Retention Rate (%) | |
|---|---|---|
| (days) | Lot No. C | Lot No. D |
| 1 | 99.1 ± 0.4 | 42.6 ± 1.9 |
| 2 | 99.0 ± 0.3 | 43.4 ± 6.6 |
| 3 | 99.2 ± 0.2 | 43.9 ± 6.8 |
| 4 | 99.2 ± 0.3 | 39.9 ± 5.7 |
| 8 | 99.3 ± 0.0 | 50.0 ± 2.1 |
| 14 | 99.5 ± 0.3 | 48.7 ± 2.7 |
| 28 | 84.7 ± 2.6 | 27.6 ± 1.3 |

As shown in Table 3, the microcapsule of the present invention prevented drug release for up to 2 weeks, with drug release confirmed at 4 weeks. This suggests that the binding between the drug having a carboxyl group and the polymer having a basic group was weakened by the formation of a new carboxyl group upon hydrolysis of the base polymer, resulting in drug release. It is therefore evident that controlling the rate of biodegradation of the polymer having the basic group would enable the setting of any duration of release.

Example 13

100 mg of 1,1-bis(4-methoxyphenyl)-1-cyano-heptanehydroxamic acid (compound B), which had a free hydroxamic acid group, and 900 mg of the polymer obtained in Example 7, which had a basic group, were dissolved in 1 ml of dichloromethane. This solution was injected to 200 ml of a 0.1% (w/v) aqueous solution of polyvinyl alcohol (Gosenol EG-40, produced by The Nippon Synthetic Chemical Industry) containing 5% (w/v) mannitol, while the solution was stirred at 7,000 rpm using a small homogenizer (Autohomomixer, produced by TOKUSHU KIKA), to yield an o/w emulsion. While the o/w emulsion was stirred at room temperature for 3 hours, the internal emulsion was then solidified by dichloromethane volatilization, after which this suspension was sieved through a 75 μm mesh sieve, then collected using a centrifuge. This was again dispersed in water and re-centrifuged; the drug released was washed away. This washing procedure was repeated in two cycles.

After 50 mg of mannitol was added, the microcapsules collected were freeze-dried to ensure solvent removal and dehydration and yield a powder (lot No. E).

For comparison, microcapsules (lot No. F) were prepared by the same method as that described above but the polymer was replaced with a PLA having a molecular weight of 12,000.

Experimental Example 3
(Release Test)

Each microcapsule preparation, 20 mg, was weighed into a 10 ml vial; 10 ml of Dulbecco's phosphate buffer (Ca/Mg-free, produced by Wako Pure Chemical Industry) containing 0.05% (w/v) Tween 80 (produced by Wako Pure Chemical Industry) and 5% (w/v) G2-β-cyclodextrin (produced by Ensuiko Sugar Refining Co., Ltd., Japan) was added; the vial was tightly stoppered. This vial was shaken at 37° C. and 120 spm; after a given period of time, a portion of this suspension was filtered; compound B was quantified by HPLC of the filtrate.

The percent ratios (entrapment ratio) of the compound B contents achieved to the contents charged for both microcapsule preparations are shown in Table 4. The percent ratios (retention rates) of the drug contents in the microcapsule during a 4-week release test to the initial contents are shown in Table 5.

TABLE 4

| Lot No. | Content (%) | Entrapment Ratio (%) |
|---|---|---|
| E | 8.64 ± 0.22 | 97.4 |
| F | 7.03 ± 0.10 | 89.2 |

TABLE 5

| Time | Retention Rate (%) | |
|---|---|---|
| (days) | Lot No. E | Lot No. F |
| 1 | 85.7 ± 0.4 | 75.1 ± 1.1 |
| 2 | 79.4 ± 0.5 | 64.9 ± 0.9 |
| 3 | 74.5 ± 0.1 | 56.4 ± 0.4 |
| 7 | 56.8 ± 0.5 | 29.3 ± 0.9 |
| 11 | 42.5 ± 0.3 | 9.1 ± 1.0 |
| 14 | 33.4 ± 0.4 | 6.7 ± 0.3 |
| 28 | 14.6 ± 2.4 | 2.5 ± 0.2 |

In the microcapsule of the present invention, initial drug release was markedly suppressed, in comparison with conventional microcapsules, demonstrating an excellent sustained release of the drug having the hydroxamic acid group.

Experimental Example 4
(In Vivo Release Test)

The microcapsules containing compound B (lot No. E), obtained in Example 13, 230.38 mg, were suspended in 11 ml of a dispersant for microcapsule administration (prepared by dissolving 50 g of mannitol, 0.5 g of carboxymethyl cellulose sodium and 2 g of polyoxyethylene(20)sorbitan monooleate (all reagents produced by Wako Pure Chemical Industry) and sterilizing under increased pressure at 120° C. for 20 minutes), and subcutaneously administered to the cervical backs of rats (Clea Japan, Inc., SD male, 7 weeks of age), previously shaven under ether anesthesia, at 0.5 ml per animal (compound B: 0.905 mg/rat, equivalent to 10.47 mg microcapsule powder/rat). Administration was achieved using a Termo syringe and the Termo injection needle Neolus. At the same time, 0.5 ml of a dosing liquid was aspirated into a syringe, as with administration, then collected in a centrifugal glass tube.

Microcapsules, previously supplemented with 10 ml of acetonitrile and 10 ml of 20 mM phosphate buffer (pH 3) in the case of the initial microcapsules, or previously supplemented with 10 ml of acetonitrile and 4 ml of 20 mM phosphate buffer (pH 3), mixed using a small homogenizer (Polytron, produced by Kinematica), and combined with washings from 2 times of homogenizer blade washing with 3 ml of 20 mM phosphate buffer (pH 3) in the case of the subcutaneously collected microcapsules, were shaken for 30 minutes (reciprocal shaker SR-2s, produced by Taitec) and centrifuged at 3,000 rpm for 10 minutes (small cooling centrifuge CF7D model, produced by Hitachi Koki Co., Ltd.); the supernatant was filtered (liquid chromatography disc 13CR 0.45 μm PTFE, produced by Gelman Sciences Japan Ltd., Japan). The resulting filtrate was analyzed by HPLC. HPLC was conducted using a chromatograph system produced by Hitachi Ltd. (L-5020 Column Oven, L-4250 UV-VIS Detector, L-6300 Intelligent Pump, AS-4000 Intelligent Auto Sampler, D-2500 Chromato Integrator) under the analytical conditions shown below.

| Column | : | Inertsil ODS-3 (GL Sciences Inc.), 4.6 mm ID × 150 mm L |
|---|---|---|
| Mobile phase | : | 20 mM phosphate buffer (pH 3)/ acetonitrile = 50/50 |
| Flow rate | : | 1.0 ml/min |
| Detection | : | 254 nm |
| Temperature | : | 40° C. |
| Sample injection volume | : | 20 μl |

For comparison, microcapsules prepared with the same formulation as that for lot No. F described in Example 13 (compound content 9.72%, entrapment ratio 108.5%) were examined for in vivo release, using the same drug dose per animal (10.63 mg microcapsule powder/rat). The changes over time in percent retention in rat subcutaneous tissue for lot Nos. E and F are shown in Table 6.

TABLE 6

| Time | Retention Rate (%)[b] | |
|---|---|---|
| (days) | Lot No. E | Lot No. F |
| 1 | 74.2 ± 2.4 | 70.4 ± 1.5 |
| 7 | 44.5 ± 0.5 | 12.2 ± 1.3 |
| 14 | 18.1 ± 1.9 | Not detected |
| 21 | 0.1 ± 0.0 | — |

[b] n = 5

In comparison with conventional microcapsules, the microcapsules of the present invention showed markedly increased release control effect even in vivo.

Example 14

To a 50 ml three-mouthed flask, 1.9522 g of 2-(N-benzyloxycarbonyl)aminoethanol and 15.0040 g of DL-lactide were added, followed by heating to 125° C. for melting. In dry nitrogen, 110 μl of a solution of tin octoate in toluene (152.5 mg/ml) was added, followed by reaction for 8 hours. The reaction product was dissolved in 110 ml of chloroform; the organic phase was repeatedly washed with water until the pH of the water phase became 6. The washed organic phase was concentrated to dryness and subsequently vacuum dried to yield 15.5673 g of a poly(DL-lactide) wherein 2-(N-benzyloxycarbonyl)aminoethanol was bound to the terminal carboxyl group via ester linkage. As determined by GPC, Mn=1,800 and Mw=2,400. The number-average molecular weight determined by $^1$H-NMR (CDCl$_3$) of the polymer on the basis of the terminal group quantitation method was 1,600.

Example 15

To a 100 ml three-mouthed flask, 0.3384 g of N-tert-butoxycarbonylaminoethanol was added, after which it was dissolved by the addition of 5 ml of toluene in dry nitrogen. While the solution was cooled with dry ice/acetone, a solution of an equal molar amount of triethylaluminum in toluene was added. After heating to 80° C., a solution of 3.9445 g of DL-lactide in 8 ml of 1,4-dioxane was added. After reaction at 90° C. for 4 days, the solvent was distilled off, followed by redissolution of the residue in 10 ml of chloroform. To this solution, 30 ml of 1 N hydrochloric acid was added, followed by stirring and liquid separation, after which the organic phase was repeatedly washed with water until the pH of the water phase became 6. The washed organic phase was concentrated to dryness and subsequently vacuum dried to yield a poly(DL-lactide) wherein N-tert-butoxycarbonylaminoethanol was bound to the terminal carboxyl group via ester linkage. As determined by GPC, Mn=3,600 and Mw=8,200. 1H-NMR (CDCl$_3$) of the polymer detected a signal for the tert-butoxy group.

Example 16

2.2 g of the polymer obtained in Example 15 was dissolved in 8 ml of chloroform and cooled with ice; 328 μl of acetic anhydride, 481 μl of triethylamine and 17 mg of dimethylaminopyridine were added, followed by reaction at room temperature for 24 hours. The reaction product was diluted with chloroform, followed by 5 cycles of water washing and liquid separation. This organic phase was concentrated to dryness and subsequently vacuum dried to yield a poly(DL-lactide) wherein the hydroxyl terminal was acetylated and wherein N-tert-butoxycarbonylaminoethanol was bound to the terminal carboxyl group via ester linkage. As determined by GPC, Mn=2,600 and Mw=5,800. $^1$H-NMR (CDCl$_3$) of the polymer detected a signal for the acetyl group.

Example 17

1.85 g of the polymer obtained in Example 16 was dissolved in 4 ml of trifluoroacetic acid, followed by stirring at room temperature for 30 minutes, after which the reaction product was added drop by drop to water to precipitate the polymer, which was then recovered. The polymer was then dissolved in chloroform and washed with a saturated aqueous solution of sodium hydrogen carbonate, followed by liquid separation, water washing and further liquid separation. This organic phase was concentrated to dryness and subsequently vacuum dried to yield a poly(DL-lactide) wherein the hydroxyl terminal was acetylated and wherein 2-aminoethanol was bound to the terminal carboxyl group via ester linkage. As determined by GPC, Mn=2,600 and Mw=5,800.

Labeling this polymer with phenyl isothiocyanate confirmed the presence of the amino group.

Example 18

To a 50 ml three-mouthed flask, 0.3224 g of N-tert-butoxycarbonylaminoethanol was added, after which it was dissolved by the addition of 1 ml of toluene in dry nitrogen. While the solution was cooled with dry ice/acetone, a solution of an equal molar amount of triethylaluminum in toluene was added. After the mixture was returned to room temperature, 3.8778 g of DL-lactide was added, followed by reaction at 130° C. for 1 hour. After the reaction product was dissolved in 80 ml of dichloromethane, 60 ml of 0.1 N hydrochloric acid was added, followed by stirring and liquid separation, after which the organic phase was repeatedly washed with water until the pH of the water phase became 6. The washed organic phase was concentrated to dryness and subsequently vacuum dried to yield a poly(DL-lactide) wherein N-tert-butoxycarbonylaminoethanol was bound to the terminal carboxyl group via ester linkage. As determined by GPC, Mn=4,400 and Mw=9,600.

Example 19

Two grams of the polymer obtained in Example 18 was dissolved in 4 ml of trifluoroacetic acid, followed by stirring at room temperature for 30 minutes, after which the reaction product was added drop by drop to water to precipitate the polymer, which was then recovered. The polymer was then dissolved in dichloromethane and washed with a saturated aqueous solution of sodium hydrogen carbonate, followed by liquid separation, water washing and further liquid separation. This organic phase was concentrated to dryness and subsequently vacuum dried to yield a poly(DL-lactide) wherein 2-aminoethanol was bound to the terminal carboxyl group via ester linkage.

Example 20

Using 1.0429 g of N,N'-bis(benzyloxycarbonyl)-1,3-diaminopropan-2-ol, 12.6172 g of DL-lactide and 3.3869 g of glycolide, a poly(DL-lactide-co-glycolide) wherein N,N'-bis(benzyloxycarbonyl)-1,3-diaminopropan-2-ol was bound to the terminal carboxy group via ester linkage was obtained by the polymerization according to the method shown in Example 10. As determined by GPC, Mn=7,300 and Mw=14,900. Mn by end-group determination is 10,800. $^1$H-NMR-(CDCl$_3$) of the polymer demonstrated L/G(mole ratio)=74.6/25.4.

Example 21

Porymelizing 1.6744 g of N,N'-bis(benzyloxycarbonyl)-1,3-diaminopropan-2-ol, 14.017 g of DL-lactide according to the method described in Example 10, a poly(DL-lactide) wherein N,N'-bis(benzyloxycarbonyl)-1,3-diaminopropan-2-ol was bound to the terminal carboxy group via ester linkage was obtained. As determined by GPC, Mn=6,200 and Mw=10,600. Mn determined from the $^1$H-NMR-(CDCl$_3$) of the polymer on the basis of the end-group determination is 4,600.

4.0404 g of the resulting polymer was subjected to deprotection reaction to yeild poly(DL-lactide) wherein 1,3-diaminopropan-2-ol was bound to the terminal carboxy group via ester linkage. Deprotection rate determined from $^1$H-NMR-(CDCl$_3$) of the polymer is 97%.

Example 22

0.396 ml triethylamine was added to a solution of 8.839 g of a lactic acid-glycolic acid copolymer (L/G 75/25 (mole %); Mn=4,926; Mw=12,450; Wako Pure Chemical) disolved in 25 ml of N,N-dimethylfolmamide under the ice cooling and cooled to −20° C. with dry ice/acetone. Then 0.343 ml of isobutylchloroformate was added, followed by stirring at −10° C. to −15° C. for 10 minutes. The resulting activated lactic acid-glycolic acid copolymer was added drop by drop to the solution which was prepared by disolving t-butyl-N-(6-aminohexyl)carbamate into 10 ml N,N-dimethylformamide and adding 0.271 ml of triethylamine beforehand under the ice-cooling, followed by stirring at room temperature for 90 minutes. After the reaction solution was concentrated under reduced pressure, 150 ml of 5% citric acid solution was added to the residue and the precipitate was obtained. The oily substance obtained by dissolving the precipitate with 40 ml chloroform and concentrated under reduced pressure was dissolve to 20 ml trifluoroacetic acid, followed by stirring under ice-cooling for 2.5 hours to remove the t-butoxycarbonyl group. The precipitate obtained by adding the reacting solution drop by drop to 200 ml cold ether was disolved to 20 ml N,N-dimethylformamide. After the resulting solution was concentrated under reduced pressure, 150 ml of 5% sodium bicarbonate solution was added. After the resulting precipitate was filtrated and washed with 5% sodium bicarbonate solution and purified water respectively, dispersed to about 30 ml of purified water and freez-dried to yield a lactic acid-glycolic acid copolymer where in a hexyldiamine was bound to the terminal carboxy group via amide linkage (yield 4.79 g). As determind by GPC, Mn=5,057 and Mw=11,644.

The solution prepared by adding phenyl isocyanate which apt to add to amino group to the chloroform solution of the resulting polymer under the presence of triethylamine was analyzed by GPC using detection wave length of 254 nm. As a result that a peak which was not appeared in the analysis of the starting material lactic acid-glycolic acid copolymer was appeared, the presence of amino group in the resulting polymer was demonstrated.

What is claimed is:

1. A sustained-release preparation which comprises a bioactive substance having an acidic group and a biodegradable polymer selected from the group consisting of biodegradable polymers (Ia)–(Ig) having the following formulae:

POLY-CO—A—X  (Ia)

wherein, in formula (Ia), POLY represents the principal chain of the biodegradable polymer: A represents O, NH or S: and X represents a hydrocarbon group having 1 to 3 amino groups,

wherein, in formula (Ib), POLY represents the principal chain of the biodegradable polymer; X represents a hydrocarbon group having 1 to 3 amino groups; and ring $A^1$ is a 5- to 7-membered ring,

wherein, in formula (Ic), POLY represents the principal chain of the biodegradable polymer: Y represents a hydrocarbon group having 1 to 3 amino groups; and ring $A^2$ is a 5- to 7-membered ring,

X—CO—O-POLY-CO—A—X  (Id)

wherein, in formula (Id), POLY represents the principal chain of the biodegradable polymer; A represents O, NH or S; and X represents a hydrocarbon group having 1 to 3 amino groups,

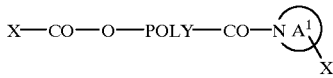 (Ie)

wherein, in formula (Ie), POLY represents the principal chain of the biodegradable polymer: X represents a hydrocarbon group having 1 to 3 amino groups: and ring $A^1$ is a 5- to 7-membered ring,

 (If)

wherein, in formula (If), POLY represents the principal chain of the biodegradable polymer; X and Y represent a hydrocarbon group having 1 to 3 amino groups: and ring $A^2$ is a 5- to 7-membered ring, and X—CO—O-POLY-CO—$R^0$ (Ig)

wherein, in formula (Ig), POLY represents the principal chain of the biodegradable polymer; X represents a hydrocarbon group having 1 to 3 amino groups; and $R^0$ represents a hydrocarbon group.

2. A biodegradable polymer selected from the group consisting of biodegradable polymers (Ia)–(Ig) having the following formulae:

POLY-CO—A—X (Ia)

wherein, in formula (Ia), POLY represents the principal chain of the biodegradable polymer other than polyamides and polyamino acids; A represents O, NH or S; and X represents a hydrocarbon group having 1 to 3 amino groups,

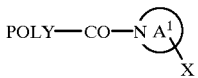 (Ib)

wherein, in formula (Ib), POLY represents the principal chain of the biodegradable polymer; X represents a hydrocarbon group having 1 to 3 amino groups; and ring $A^1$ is a 5- to 7-membered ring,

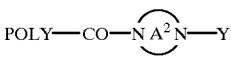 (Ic)

wherein, in formula (Ic), POLY represents the principal chain of the biodegradable polymer; Y represents a hydrocarbon group having 1 to 3 amino groups; and ring $A^2$ is a 5- to 7-membered ring, X—CO—O-POLY-CO—A—X (Id)

wherein, in formula (Id), POLY represents the principal chain of the biodegradable polymer other than polyamides and polyamino acids; A represents O, NH or S; and X represents a hydrocarbon group having 1 to 3 amino groups,

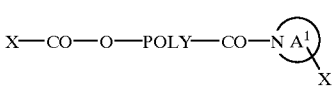 (Ie)

wherein, in formula (Ie), POLY represents the principal chain of the biodegradable polymer, X represents a hydrocarbon group having 1 to 3 amino groups; and ring $A^1$ is a 5- to 7-membered ring,

 (If)

wherein, in formula (If), POLY represents the principal chain of the biodegradable polymer; X and Y represent a hydrocarbon group having 1 to 3 amino groups; and ring $A^2$ is a 5- to 7-membered ring, and X—CO—O-POLY-CO—$R^0$ (Ig)

wherein, in formula (Ig), POLY represents the principal chain of the biodegradable polymer; X represents a hydrocarbon group having 1 to 3 amino groups; and $R^0$ represents a hydrocarbon group.

3. The biodegradable polymer as claimed in claim 2, wherein, in formulas (Ia) and (Id), the POLY represents the principle chain of the biodegradable polymer selected from the group consisting of fatty acid polyesters, polyanhydrides, polycarbonates, poly-ortho-esters, poly-α-cyanoacrylic acid esters, polyphosphazenes and polydepsipeptides.

* * * * *